United States Patent [19]
Hargest

[11] 3,938,513
[45] Feb. 17, 1976

[54] SYRINGE FILTER AND VALVE COMBINATION

[76] Inventor: Thomas S. Hargest, 1078 Winslow Drive, Charleston, S.C. 29412

[22] Filed: Jan. 3, 1974

[21] Appl. No.: 430,418

[52] U.S. Cl. .................. 128/218 R; 128/218 NV
[51] Int. Cl.² ..................................... A61M 5/00
[58] Field of Search ......... 128/221, 218 N, 218 NV, 128/215, 218 M

[56] References Cited
UNITED STATES PATENTS

| | | | |
|---|---|---|---|
| 1,363,128 | 12/1920 | Kitaoka | 128/218 NV |
| 2,893,390 | 7/1959 | Lockhart | 128/218 NV |
| 3,075,525 | 1/1963 | McConnaughey | 128/218 NV |
| 3,089,490 | 5/1963 | Goldberg | 128/218 NV |
| 3,370,754 | 2/1968 | Cook et al. | 128/218 M X |
| 3,373,743 | 3/1968 | Saffir | 128/218 NV |
| 3,477,432 | 11/1969 | Shaw | 128/218 M |
| 3,736,932 | 6/1973 | Satchell | 128/218 R |
| 3,747,812 | 7/1973 | Karman et al. | 128/218 NV X |

FOREIGN PATENTS OR APPLICATIONS 733,447  10/1932  France ........................ 128/218 M

*Primary Examiner*—John D. Yasko
*Attorney, Agent, or Firm*—Dawson, Tilton, Fallon & Lungmus

[57] ABSTRACT

An improved filter and valve assembly used in combination with a medical syringe for blocking, and thereby protecting a patient against, the infusion of particulate matter. The filter element is fixed within the bore of the syringe and a tubular valve body is secured within a central opening in the filter element. A flexible closure formed integrally with the tubular valve body opens and closes the valve passage, which serves as a filter by-pass, when the plunger of the syringe is raised (withdrawn) and lowered (depressed).

11 Claims, 5 Drawing Figures

U.S. Patent  Feb 17, 1976  3,938,513
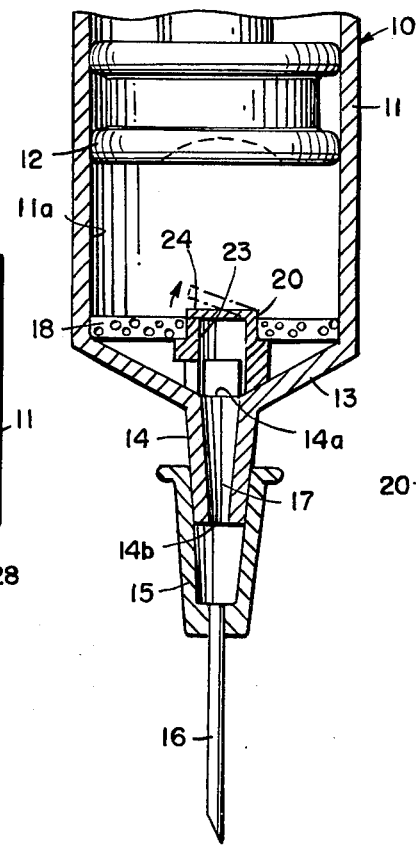
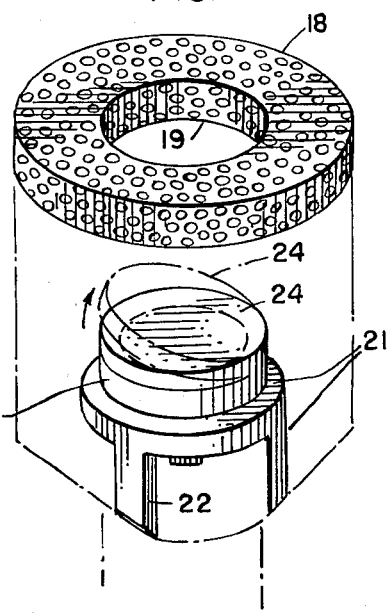
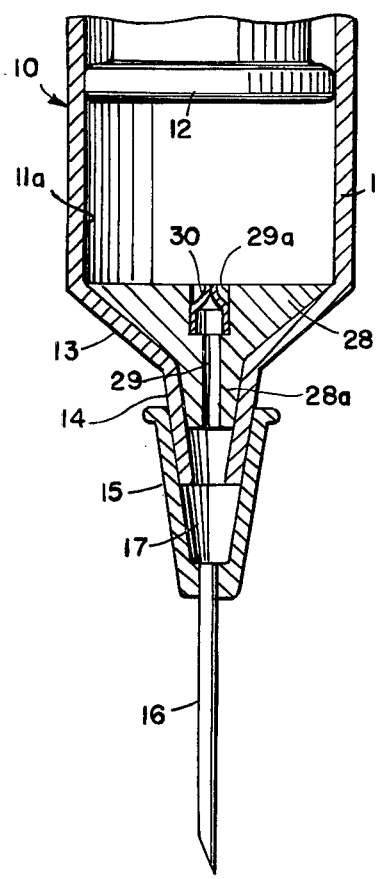
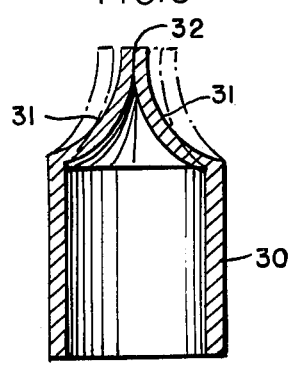
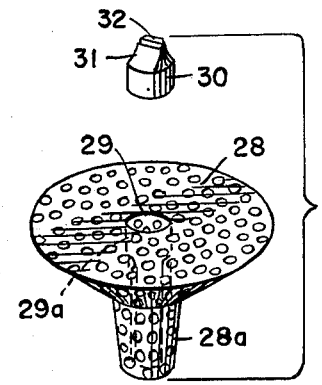

3,938,513

SYRINGE FILTER AND VALVE COMBINATION

BACKGROUND

U.S. Pat. No. 3,757,780 discloses a needle assembly for use with a syringe or other type of medical injector, the needle assembly including a movable filter element which shifts axially within the hub of the needle depending on the direction of liquid flow therethrough. To withstand such movement and the forces generated by fluid flowing through the hub, particularly as such fluid is being drawn into the syringe, the filter element or disc must be formed of a relatively rigid unyielding material, thereby severely limiting the selection of materials suitable for use in a structure having a movable filter.

Other patents illustrating the state of the art are U.S. Pat. Nos. 3,757,779, 3,736,932, 3,722,697, 3,449,081, 1,539,314, 964,730, and 128,257.

SUMMARY

An important aspect of the present invention lies in providing a syringe filter and valve combination having a by-pass function without at the same time being restricted to the use of rigid filter materials. Conventional filter materials of non-rigid character, such as non-woven materials, are suitable because the filter element is fixed in position within the syringe body. A valve, having a tubular valve body, extends centrally through the filter element and provides a passage for the preferential flow of fluid into the barrel of the syringe when the plunger is drawn outwardly or lifted. A flexible closure, preferably formed integrally with the valve body, is positioned at the upper end of the valve passage and closes that passage upon reversal of fluid flow. The injection fluid therefore follow a less direct route, passing through the immovable filter element as that fluid is forced by the plunger towards the needle mounted at the end of the syringe body.

In one form of the invention, the tubular valve body coacts with the syringe barrel to support the filter element within the bore of the syringe. The valve closure element may comprise an imperforate disc hinged to the upper end of the tubular valve body, the disc being larger than the diameter of the valve passage and seating against the upper end of the valve body to block the discharge of fluid through the valve passage, or it may comprise a flap arrangement formed at the upper end of the body, one of the paired flaps engaging the other to block the outflow of fluid through the valve passage when the syringe plunger is thrust inwardly or downwardly. Thus, in one case the closure element is braced in its closed position by the upper end of the valve body and, in the other case, by the opposing flap.

Other advantages, objects and features of the invention will become apparent as the specification proceeds.

DRAWINGS

FIG. 1 is a vertical sectional view of the lower portion of a syringe equipped with the filter-valve assembly of the present invention.

FIG. 2 is an exploded perspective view illustrating the filter and valve components.

FIG. 3 is a sectional view of a syringe similar to FIG. 1 but illustrating a second form of the filter-valve assembly.

FIG. 4 is an exploded perspective view of the filter and valve shown in FIG. 3.

FIG. 5 is an enlarged longitudinal sectional view of the valve structure of FIGS. 3 and 4.

DESCRIPTION

Referring to FIGS. 1 and 2, the numeral 10 generally designates a syringe having a syringe barrel 11 and a reciprocable plunger 12. The barrel is provided with a cylindrical bore 11a and has a bottom wall 13 merging with a reduced downwardly projecting neck portion 14. The neck is adapted to be coupled with the hub 15 of a conventional hypodermic needle 16. Since all of the structure so far described is entirely conventional and well known in the art, a more detailed description is believed unnecessary herein. A simple friction fit between the hub 15 and neck 14 is illustrated but other types of connections, such as a conventional Luer lock, may be used. Similarly, while end wall 13 is shown to be of sloping or frustoconical shape, other configurations, including simply a flat or planar end wall, might be provided.

An axial flow passage 17 extends between the upper and lower ends 14a and 14b of the neck. The flow passage of the neck is preferably coaxial with the cylindrical bore 11a and communicates with both the bore and the interior of needle hub 15.

Filter element 18 is annular in shape and is dimensioned to fit tightly within the lower portion of bore 11a. As shown most clearly in FIG. 2, the filter element has an axial or central opening 19 extending therethrough. If desired, the filter may be formed of a relatively rigid material, such as sintered particles of plastic (such as polypropylene or polyethylene) but, as indicated above, a particularly advantageous aspect of the invention lies in the fact that non-rigid filtering materials, such as conventional non-woven fibrous materials, may be used. In most instances a tight frictional fit between the periphery of the filter and the inside wall of the barrel is believed sufficient to secure the filter in place as shown in FIG. 1; however, with highly flexible or resilient filter materials, it may be desirable to attach the periphery of the filter to the cylindrical bore by cement or by any other suitable attachment means. In any event, the filter element is formed of a foraminous material which has micropores of a sufficiently small size to block the passage therethrough of any particulate material considered objectionable in an injectable solution.

A tubular valve body 20 extends through the central opening 19 of the filter and has its cylindrical outer wall partly secured or sealed to the filter. An annular shoulder 21 bears against the undersurface of the filter to help support that filter as well as to contribute in blocking the passage of particulate matter along the central opening 19 where the filter material interfaces with the cylindrical surface of the valve body. The lower portion of the tubular valve body is provided with enlarged side openings 22 and, as shown in FIG. 1, the bottom of that body rests upon bottom wall 13 of the syringe.

The central passage 23 of the tubular valve body is in direct alignment with flow passage 17 of neck 14. At the upper end of the valve body is a disc-shaped closure 24 which is formed intergrally with the valve body and is joined thereto by hinge portion 25. When the closure is in its lowered or closed position as shown in solid lines in FIGS. 1 and 2, it seats or rests upon the upper end surface of the tubular valve body. The closure 24 is normally in an unflexed closed condition; however, when fluid flows upwardly through valve passage 23 in response to lifting or withdrawal movement of the plunger, the closure flexes upwardly into the open or raised position indicated in the drawings by broken lines.

When the plunger is raised, fluid flowing upwardly through needle 16 and hub 15 tends to pass into the bore of the syringe through the flow passage 23 of the valve body rather than through porous filter 18, partly because of the direct axial alignment between the flow passages of the valve body and neck and partly because closure 24 readily flexes upwardly into its broken-line position. Thus, particulate matter entrained in the fluid drawn into the syringe will tend to pass directly through the flow passage of the valve body rather than engage, and be restrained by, the undersurface of filter element 18. When the direction of movement of the plunger is reversed, the imperforate closure 24 returns to its normally closed position and fluid discharged from the syringe must pass through the filter element. Thus, the filter blocks the return flow of such particulate matter.

In the variation illustrated in FIGS. 3-5, the parts are essentially the same except for differences in the construction of the filter and valve. Filter 28 may be formed from any of the materials used in the fabrication of filter 18. The annular filter 28 has a central opening 29 extending axially therethrough. The undersurface of the filter element may be of frusto-conical shape to conform with the configuration of end wall 13 and, if desired, the filter element may be provided with a depending extension 28a received within the flow passage of neck 15. A tight frictional fit may be sufficient to secure the filter element within the lower end of the bore but, if additional holding force is required, an adhesive or any other suitable attachment means may be used.

The upper end of bore 29 is preferably enlarged at 29a to receive the tubular valve body 30. As shown in the drawings, the lower portion of the body 30 is generally cylindrical in shape. The upper portion is transversely flattened to provide a pair of opposing flap portions 31 which normally engage each other along a transverse seal line 32. The upstanding side edges of the respective flaps may be separable although preferably the flap elements of the closure are joined together along those edges. Normally the flaps assume the closed condition shown in solid lines in FIG. 5; however, when fluid is drawn into the syringe the upper edges of the flaps spread apart to permit such upward flow.

The body of the tubular valve may be secured in place within counter-bore 29a by friction or, if necessary, by adhesives, heat sealing, or any other suitable attachment means. Like valve body 20 and closure 24, valve body 30 and its integral closure means 31 may be formed of any suitable flexible material, preferably an inert plastic material selected from any of a variety of such materials well known in the art.

While in the foregoing certain embodiments of the invention have been disclosed in considerable detail for purposes of illustration, it will be understood that such details may be varied considerably without departing from the spirit and scope of the invention.

I claim:

1. A syringe having a barrel and a plunger slidable therein, said barrel having a cylindrical bore and having a bottom wall provided with an axially and downwardly projecting neck portion for rigid attachment to an injection needle, said neck portion having an axial flow passage communicating with said bore, wherein the improvement comprises an annular filter element fixed within said bore adjacent said bottom wall, said filter element being formed from foraminous material capable of filtering objectionable particulate matter from injectable fluids, said filter element having a central opening extending therethrough, and a tubular valve body secured within said central opening having an axial valve passage and having a normally-closed one-way valve closure element disposed at the upper end of said valve passage and spaced a substantial distance upwardly from said neck portion, said closure element being flexible between an open position and a normal closed position, and means bracing said closure element in said closed position and preventing movement of said closure element into said open position in response to greater fluid pressures above said filter element than below the same, whereby, said closure element and said bracing means cooperate to block downward flow through said passage when said plunger is urged downwardly and to permit upward flow through said passage when said plunger is raised.

2. The syringe of claim 1 in which said valve closure element is formed integrally with said body.

3. The syringe of claim 2 in which said closure element and valve body are formed integrally from flexible plastic material.

4. The syringe of claim 1 in which said valve body engages said bottom wall and supports said filter element within said bore.

5. The syringe of claim 4 in which said tubular valve body is provided with side openings adjacent the lower end thereof for the flow of fluid laterally therethrough.

6. The syringe of claim 4 in which said valve body is provided with an annular shoulder spaced below said closure element, said shoulder having lateral dimensions greater than the central opening of said filter element and engaging the underside of said filter element for supporting the same within said bore.

7. The syringe of claim 6 in which said annular shoulder has transverse dimensions smaller than the diameter of said bore.

8. The syringe of claim 3 in which said closure element comprises an imperforate disc hinged to the upper end of said tubular valve body and having a diameter larger than that of said valve passage.

9. The syringe of claim 3 in which said closure element and said bracing means comprise a pair of flaps projecting upwardly and inwardly from the upper end of said valve body, said flaps being engagable with each other for sealing said opening to block the downward flow of fluid through said valve passage.

10. The syringe of claim 9 in which said flaps are hingedly connected to each other along opposite side edges.

11. A syringe comprising a barrel and a plunger slidable therein, said barrel having a cylindrical bore and having a bottom wall provided with an axially and downwardly projecting neck portion having an axial flow passage communicating with said bore, an injection needle rigidly attached to said neck portion, an annular filter element fixed within said bore adjacent said bottom wall, said filter element being formed from foraminous material capable of filtering objectionable particulate matter from injectable fluids, said filter element having a central opening extending therethrough and a tubular valve body secured within said central opening having an axial valve passage and having a flexible normally-closed valve closure element at the upper end of said valve passage spaced a substantial distance upwardly from said neck portion, said closure element being movable between a flexed open position and a normal closed position, means bracing said closure element in its closed position and preventing movement of said closure element into said open position in response to greater fluid pressures above said filter element than below the same, whereby, said closure element and said bracing means cooperate in automatically blocking downward flow through said passage when said plunger is urged downwardly and in permitting upward flow through said passage when said plunger is raised.

* * * * *